United States Patent [19]

Marck et al.

[11] E Patent Number: Re. 33,194

[45] Reissued Date of Patent: Apr. 10, 1990

[54] [ADJUSTABLE ORTHOPEDIC SHOE FOR TREATING FOOT MALFORMATIONS IN INFANTS] *ORTHOPEDIC DEVICE FOR ALIGNING JOINTS*

[76] Inventors: Thierry Marck, Le Clos des Bax Quai Warrens; Gerard M. Dumoutier, 13 Rue des Allobroges, both of 74700 Sallanches, France

[21] Appl. No.: 239,694

[22] Filed: Sep. 2, 1988

Related U.S. Patent Documents

Reissue of:

[64] Patent No.: 4,608,970
Issued: Sep. 2, 1986
Appl. No.: 711,571
Filed: Jul. 2, 1984

[30] Foreign Application Priority Data

Jul. 4, 1983 [FR] France ..... 83 11779

[51] Int. Cl.[4] ..... A61F 5/00

[52] U.S. Cl. ..... 128/80 J; 128/584; 128/88

[58] Field of Search ..... 128/80 J, 80 A, 80 R, 128/80 C, 581, 583, 584, 585, 596, 87 C, 88; 403/56, 57, 90; 623/48, 49

[56] References Cited

U.S. PATENT DOCUMENTS

| | | | |
|---|---|---|---|
| 5,393 | 12/1847 | Chamberlin | 128/80 J |
| 483,311 | 9/1892 | Remaly | 403/90 X |
| 2,967,360 | 1/1961 | Rice | 128/80 J X |
| 3,086,522 | 4/1963 | Frohmader | 128/80 J |
| 3,171,407 | 3/1965 | Rogers | 128/80 J |
| 3,400,408 | 9/1968 | Garcia | 623/49 X |
| 3,790,965 | 2/1974 | Gelbenegger | 403/90 X |
| 3,842,187 | 10/1974 | Barkan | 403/56 X |
| 3,892,231 | 7/1975 | Tummillo | 128/80 A |
| 4,256,097 | 3/1981 | Willis | 128/80 F X |
| 4,538,599 | 9/1985 | Lindemann | 128/80 A |
| 4,677,971 | 7/1987 | Lindemann | 128/87 R |

FOREIGN PATENT DOCUMENTS

| | | | |
|---|---|---|---|
| 2744445 | 4/1979 | Fed. Rep. of Germany | 128/80 J |
| 2321267 | 3/1977 | France | 128/80 J |
| 477724 | 8/1975 | U.S.S.R. | 128/80 J |
| 940767 | 2/1982 | U.S.S.R. | 128/87 C |

*Primary Examiner*—Clifford D. Crowder
*Attorney, Agent, or Firm*—Collard, Roe & Galgano

[57] ABSTRACT

*An orthopedic device for aligning joints, especially intended as an* [The] orthopedic shoe designed for correcting malformations of the foot in infants comprises a rigid posterior part (4) to hold the hindfoot and an interior part (10) to hold the forefoot. These parts 4, 10 are secured to each other through a connecting piece (15) jointed with a ball-and-socket (19) in at least one of the parts (10) and which can be blocked (21) in position. The joint which has three degrees of freedom in the relative position of the posterior (4) and anterior (10) parts permits any adjustment to correct a malformation in the horizontal, vertical and oblique planes, whether or not accompanied by a component of torsion around the direction of deviation.

9 Claims, 4 Drawing Sheets

Figure 3:
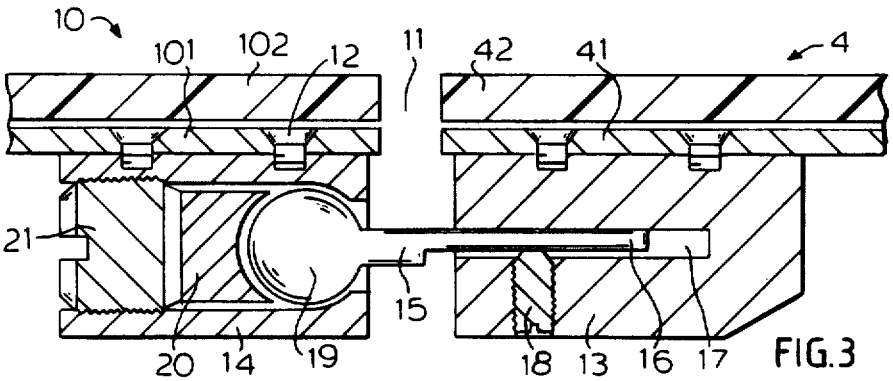

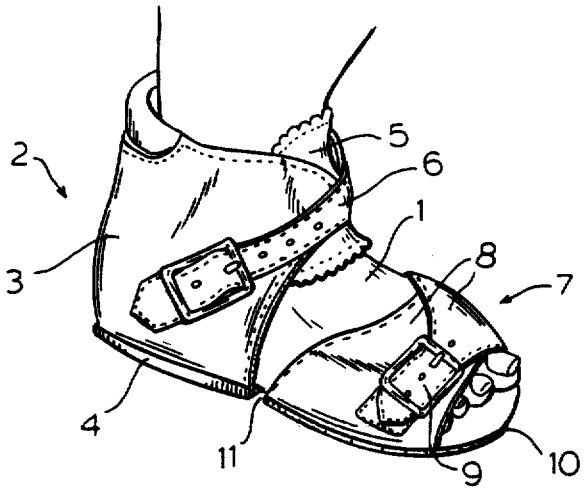
FIG.1
FIG.2
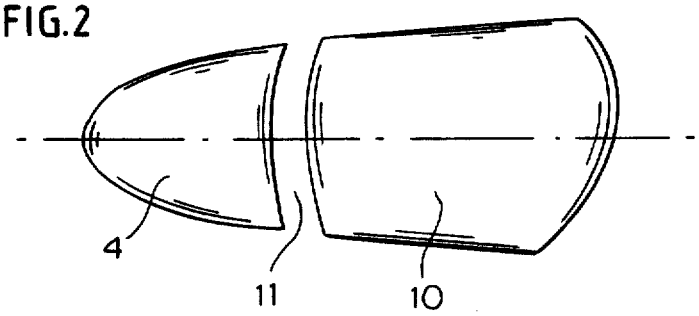

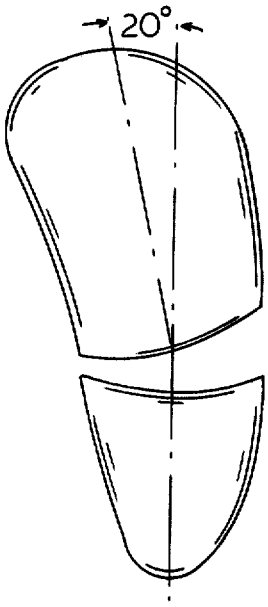
FIG.5B
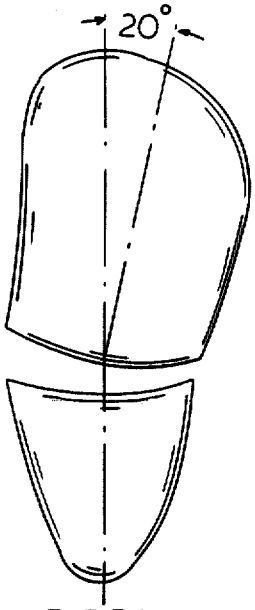
FIG.5A
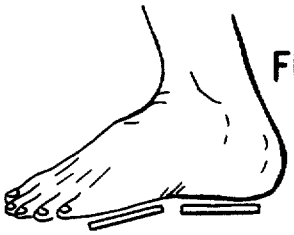
FIG.5C
FIG.5D
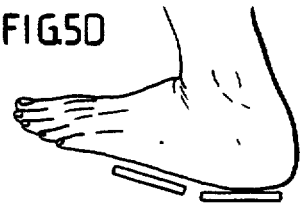
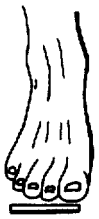
FIG.5E
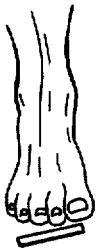
FIG.5F
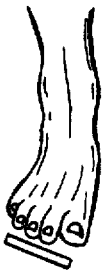
FIG.5G

[ADJUSTABLE ORTHOPEDIC SHOE FOR TREATING FOOT MALFORMATIONS IN INFANTS] *ORTHOPEDIC DEVICE FOR ALIGNING JOINTS*

Matter enclosed in heavy brackets [ ] appears in the original patent but forms no part of this reissue specification; matter printed in italics indicates the additions made by reissue.

The invention relates to orthopedic shoes designed for correcting malformations and malpositions of the feet of infants from the first days of life.

We know that a very large proportion of newborn, estimated to be of the order of 5 to 10%, are afflicted with various malformations and malpositions of the feet: talipes calcaneus, talipes valgus, talipes varus, pes adductus, talipes calcaneovalgus, talipes calcaneovarus, talipes equinovarus, metatarsus varus, pes cavus, congenital convex pes valgus, etc. Sequelae of clubfoot are also encountered frequently after the first corrective treatments.

Numerous orthopedic and therapeutic methods and techniques are currently used to reduce these deformities by the first days after birth. They include elastic adhesive bandages, so-called Finck bandages, plaster casts, [splits] *splints*, materials that can be formed by the application of heat, and, during the consolidation treatment, various types of orthopedic shoes such as shoes for correcting pes adductus, so-called American sandals, and ankle boots for correcting talipes varus.

Irrespective of the quality of the results that can be obtained, these treatments present significant disadvantages:

- repeated and varied medical procedures whose success depends to a large extent on the training, practice and skill of the practitioner;
- the unavoidable use of multiple materials and methods of implementation for the treatment of a single type of deformity;
- a high risk of trophic disorders thay may remain hidden too long and thus become irreversible, caused by the use of plaster casts, heat-formed materials, and elastic adhesive bandages;
- the existing orthopedic shoes such as American sandals, ankle boots for talipes varus and pes adductus, are applicable for only a simple type of malformation, whereas most of the time the malformation is of a combined type with variable degrees of deviations in several directions. Thus, the anti-adductor ankle boot described in French Pat. No. 2 467 560 is comprised of two separate parts corresponding respectively to the hindfoot and the forefoot, articulated around a common vertical axis and can be used effectively only on simple pes adductus, since the two parts can pivot in relation to each other only in a horizontal plane. Furthermore, in this case, there is a return spring that is supposed to exert the corrective action, and the two parts, rear and front, therefore cannot be immobilized positively in relation to each other in the desired correction position.

In the shoe proposed in U.S. Pat. No. 3,171,407, where in addition to the articulation around a vertical axis which is found in a different form, the design is furthermore concerned with a correction around two other axes that are supposed to correspond to two other degrees of freedom, this correction is theoretically realizable only by deforming as necessary a connecting piece consisting of two parallel branches. Aside from the fact that this imposed deformation can only be done empirically by applying an effort "by guesswork", that is to say, without even the most elementary precision, the two axes being practically undefinable geometrically and mechanically, which is also true of the actual extent of the deformation; this deformation is of the plastic type, and therefore irreversible, and the deformed part cannot really be used more than once or twice without being severely damaged, which must necessitate numerous replacements requiring the disassembly and reassembly of numerous parts. Also, the device that is described is extremely complex, which can hardly make its realization and use practical possibilities.

The present invention seeks to free itself of the inadequacies of the state of the art that have just been mentioned by proposing an orthopedic shoe that can be put on rapidly and makes it possible to correct the different types of malformations that can be encountered, simple or combined in several directions, without resorting to other materials.

Figure 4A:
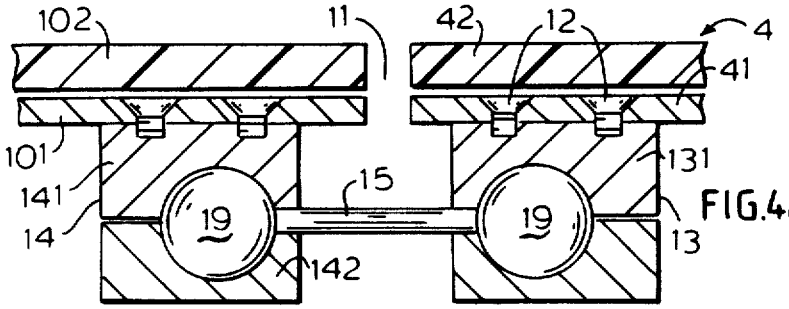
Figure 4B:
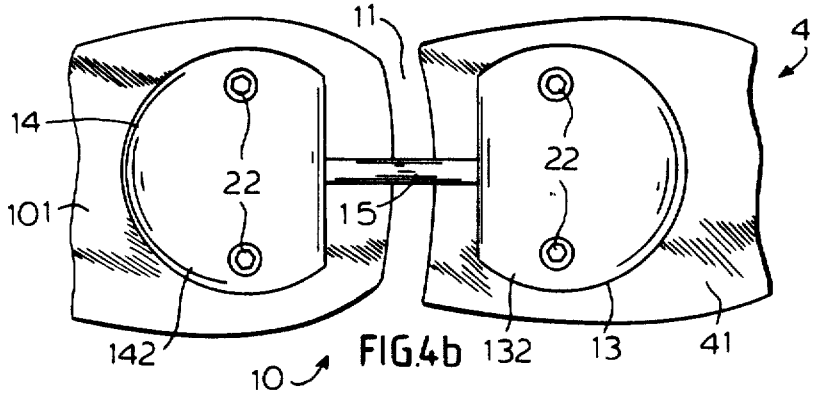

The invention, whose technical characteristics are listed in the claims, is set forth in the description that follows, for the clearer comprehension of which we shall refer to the drawings in which:

FIG. 1 represents, in perspective and generally, a shoe to which the invention is applied, FIG. 2 shows a plan view of two half-soles corresponding to the shoe in FIG. 1, FIG. 3 is a partial longitudinal section illustrating the first form of embodiment of the connection between the aforementioned half-soles pursuant to the invention, FIGS. 4a and 4b are a longitudinal section and a view from below, respectively, showing a second form of embodiment of the invention, and FIGS. 5A, B, C, D, E, F and G show a number of classic malformations that the invention can correct.

Figure 6A:
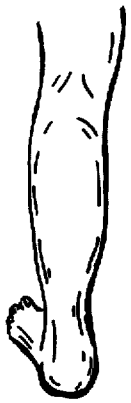
Figure 6B:
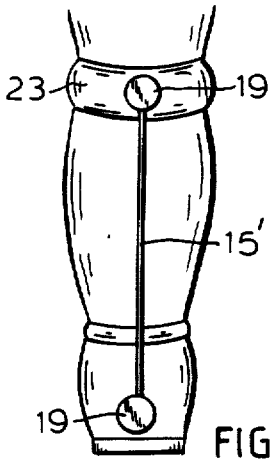
Figure 7:
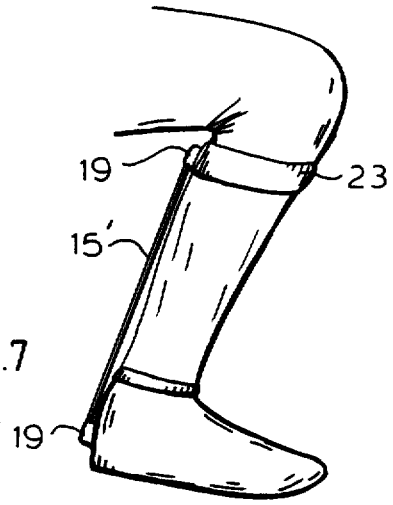

FIGS. 6A, 6B and 7 represent respectively a clubfoot seen from the rear, an application of the invention for its correction, also seen from the rear, and a side view.

In FIG. 1, we see foot 1 of an infant wearing an orthopedic [show] *shoe* to which the invention can be applied and whose essential elements which are not visible are described further on. The shoe includes two distinct separate parts. A posterior part 2, made up conventionally of a rigid ankle cuff 3 mounted on a posterior half-sole 4 with a tongue 5 and a tying strap 6 serves to hold the hindfoot firmly and comfortably. An anterior part 7 that serves to hold the forefoot has two lateral flaps with a tying strap 9 mounted on an anterior half-sole 10. The two half-soles 4 and 10 constitute two distinct elements separated by a gap or clearance 11. This clearance 11 allows a relative displacement, at least to some extent, of the two parts 2 and 7 without overlap of the half-soles 4 and 10.

FIG. 2 shows a plan view of a possible form and the relative arrangement of the two half-soles 4, 10 in an ideal position for a foot that has no deviation from the mid-vertical plane. The half-soles 4, 10 essentially include a rigid core 41, 101, preferably made of brass or aluminum, whose upper surface is covered by a lining, for example cemented, adequate for purposes of comfort 42, 102, as we see in a sectional view in FIG. 3.

The method for correcting a malformation of the foot consists in placing the two parts, anterior 7 and posterior 2, in a relative position that will encounter the malformation, and then immobilizing the two parts 2, 7, in this position. This correction must be made gradually and progressively in space and time to restore a normal anatomical and physiological situation, and therefore the degree of the relative displacements of the two parts, anterior 7 and posterior 2, must be able to be varied at will by the practitioner, at least within a certain range. In addition, as stated previously, the aim is to correct not only malformations in relation to the vertical plane (pes adductus for example) but also deviations from the horizontal plane and combined malformations, which are therefore oblique in relation to these two planes at the same time. Thus, it is necessary to provide for the relative displacement of the two parts, anterior 7 and posterior 2, with at least two degrees of freedom. Since in addition the malformations may also have a component of torsion around a longitudinal axis in relation to the foot, it is necessary to provide for at least one additional degree of freedom.

In the form of embodiment represented in a partial longitudinal section in FIG. 3, each half-sole, 4, 10, or rather its core 41, 101, is firmly connected, for example by means of screw 12, with a metal organ, 13 and 14 respectively, cooperating with a connecting piece 15 in the form of a single rod to secure the two half-soles 4, 10 to each other. These organs 13, 14 can be partially buried in the corresponding half-soles 4, 10. In the form of embodiment that is illustrated, extremity 16 of rod 15 cooperating with part 13 of the posterior portion 2 of the shoe can be moved in a recess 17 in a longitudinal movement of translation and stopped in position, for example by a screw 18, in a way which itself is known.

At its other extremity, cooperating with part 14 associated with the anterior portion 7 of the shoe, the rod or connecting part 15 has a spherical part 19 cooperating with a corresponding spherical cup formed partly in part 14 and partly in a block 20 which may tighten more or less tightly against sphere 19 through a logitudinal screw device 21 housed in part 14. Thus, we have a ball-and-socket that permits, at least to some extent, any rotational displacement of half-sole 10 around the center of sphere 19, a displacement that can be analyzed into its three components of rotation around the vertical axis, the normal horizontal axis to rod 15, and the axis of rod 15. Thus, this half-sole 10 has three degrees of freedom in relation to half-sole 4. Screw 21 acts as a brake on these displacements to help the practitioner achieve a correct positioning and then serves to block the unit in the adjustment position that is obtained, without ever having any deformation of rod 15.

In another form of embodiment represented in FIG. 4, each extremity of connecting rod 15 has a spherical part cooperating with a spherical cup formed in each metallic part 13 and 14 respectively. The braking and blocking design through the previously described longitudinal axis block could be applied here, but, as represented, it appears more advantageous to define the spherical cups in terms of two half-shells, 131, 132 and 141, 142 respectively, the first one being integral with core 41, 101 of the corresponding half-sole 4, 10 in the same manner as previously, and the second 132, 142 being fastened to the first one by means of at least one screw 22 whose degree of tightening, by pushing the shells 131, 132 and 141, 142 on spheres 19, will make it possible to brake the relative displacements of each half-sole around the center of the sphere 19 concerned and to block the unit in the desired position. This design with three degrees of freedom for each extremity of rod 15 gives greater flexibility in the search for the correction position best suited for the particular case, and still without deformation of rod 15.

In the first form of embodiment described, clearance 11 can be adjusted with a single rod 15 so that it will correspond to the right shoe size in the particular case. In contrast, in the second form, this adjustment can be made by means of rods 15 of different lengths, this part being easily interchangeable.

Other mechanically equivalent designs can of course be adopted to achieve the same result. A suitable covering can mask the greater part of the device under the shoe, and even all of it following the adjustment if it is removable.

As an illustrating example, FIG. 5 shows a number of classic malformations in the case of a right foot which the device according to the invention makes it possible to correct, and the angle of deviation may be as high as about 20° in each direction. Thus, in A, we have an opening of the foot (outward), in B a closing of the foot (inward), in C a lowering of the forefoot, in D a raising of the forefoot, and in E, F and G a foot whose position is, respectively, horizontal, inclined to the right, and inclined to the left. Positions A and B can be done in position E or can be achieved simultaneously with C and D and/or F and G as a result of the three degrees of freedom available. These different positions are always in relation to a fixed reference point.

Furthermore, for practical reasons during use, a device can be provided among the organs of the joint which is not directly accessible to the practitioner and will render the different parts inseparable in case of a clumsy move with excessive unlocking, which will prevent them from being scattered. Any design known in the art may be used for this purpose.

In addition, the explanations that have just been given can be applied, mutatis mutandis, to means for correcting malformations of the ankle joint, whether or not they are combined with malformations of the foot. Thus, FIGS. 6A, 6B and 7 illustrate very schematically the treatment of a clubfoot (FIG. 6A) by adding to the previous shoe a connecting part 15' similar to part 15 (slightly longer), secured respectively to the heel of the shoe and to a collar 23, made for example of leather, enclosing the leg of the subject below and above the knee. Extremities 19 of connecting part 15', not shown in detail, may be identical in terms of their form and their adjustable attachment with the heel and collar 23 to extremities 16 and 19 of part 15 described previously.

What is claimed is:

1. An orthopedic shoe for correcting foot malformations in infants, comprising:

(a) a rigid [posterior] *first* part;

(b) a rigid [anterior] *second* part [separate] *separated* from said [posterior] *first* part *by a clearance without overlapping*;

(c) a connecting [piece] *rod* interconnecting and securing with respect to one another said [posterior] *first* and [anterior] *second* parts, said connecting [piece being in the form of a] rod having [a first end associated with said posterior part and a second end associated with said anterior part; and, (d) means associated with said rod which, without deforming the rod, permits relative displacement with at least three degrees of freedom of said posterior and anterior parts and which is securable to immobilize said parts in position] *at its both ends a spherical part which cooperates with a spherical cup disposed in the one of said rigid first or second parts associated with said rod end and forming a ball and socket joint therein.*

[2. The shoe according to claim 1, wherein said posterior and anterior parts each include a half-sole which are separated from each other by a clearance which allows relative displacement between said half-soles without overlapping.]

[3. The shoe according to claim 2, wherein at least one of said half-soles includes said means associated with said rod which permits relative displacement.]

[4. The shoe according to claim 2, wherein said means associated with said rod which permits relative displacement includes a spherical part at least at one of the ends of said rod, said spherical part cooperating with a spherical cup disposed in the half-sole associated with said rod end and forming a ball and socket joint therein.]

5. The shoe according to claim [4] *1*, wherein said spherical cup comprises at least two [complimentary] *complementary* shells which can be tightened against each other, thereby permitting said spherical cup to clamp said spherical part to immobilize said *ball and socket* joint, or to release said spherical part to allow relative displacement between said [half-soles] *first and second parts.*

[6. The shoe according to claim 4, wherein one of the ends of said rod includes said spherical part, and the other end of said rod is longitudinally adjustable relative to the half-sole associated therewith.]

[7. The shoe according to claim 4, wherein said rod includes a spherical part at both of its ends, and each half-sole includes a spherical cup corresponding to said each spherical part.]

8. The shoe according to claim 1, wherein said connecting [part] *rod* is interchangeable with other connecting [parts] *rods* of different sizes.

[9. The shoe according to claim 1, which further includes:

(a) a collar secured around the user's leg;

(b) a connecting part interconnecting and securing said posterior part with said collar; and (c) means permitting relative displacement of said posterior part and said collar with respect to each other.]

[10. The shoe according to claim 1, wherein said means associated with said rod which permits relative displacement permits relative movement between said collar and said posterior part with at least three degrees of freedom.]

[11. The shoe according to claim 1, wherein said connecting part comprises a rod and said means associated with said rod which permits relative displacement comprises a spherical part at the end of said rod associated with said posterior part, a spherical cup disposed in said posterior part for receiving said spherical part, and means for clamping said spherical part in said spherical cup.]

12. The shoe according to claim [4] *1*, wherein said [means associated with said rod which permits relative displacement further] *ball and socket joint* comprises:

*a housing mounted on said rigid first and second parts, said spherical cup being formed within said housing;* a movable block disposed in said [half-sole] housing [said ball and socket joint] and moveable against said spherical part to clamp the same in said spherical cup; and a screw threadably received in said [half-sole] housing [said ball and socket joint,] said screw being adapted to move said block to clamp said spherical part in said spherical cup.

*13. An orthopedic device for aligning joints comprising:*

(a) a rigid first part;

(b) a rigid second part separated from said first part by a clearance without overlapping;

(c) a connecting rod interconnecting and securing with respect to one another said first and second parts, said connecting rod having at its both ends a spherical part which cooperates with a spherical cup disposed in the one of said rigid first or second parts associated with said rod end and forming a ball and socket joint therein.

*14. The device according to claim 13, wherein said spherical cup comprises at least two complementary shells which can be tightened against each other, thereby permitting said spherical cup to clamp said spherical part to immobilize said ball and socket joint, or to release said spherical part to allow relative displacement between said rigid first and second parts.*

*15. The device according to claim 13, wherein said connecting rod is interchangeable with other connecting rods of different sizes.*

*16. The device according to claim 13, which further includes:*

(a) a collar adapted to be secured around a portion of the user's body;

(b) a connecting part interconnecting and securing said rigid first or second part with said collar; and, (c) means permitting relative displacement of said first or second part and said collar with respect to each other.

*17. The device according to claim 13, wherein said ball and socket joint comprises:* a housing mounted on said rigid first and second parts, said spherical cup being formed within said housing;

a movable block disposed in said housing and moveable against said spherical part to clamp the same in said spherical cup; and, a screw threadably received in said housing and moveable against said spherical part to clamp said spherical part in said spherical cup.

* * * * *